United States Patent
Shams et al.

(10) Patent No.: US 9,943,510 B2
(45) Date of Patent: *Apr. 17, 2018

(54) PHARMACEUTICAL FORMULATIONS COMPRISING A PYRIDYLAMINOACETIC ACID COMPOUND

(71) Applicant: SANTEN PHARMACEUTICAL CO., LTD., Osaka-shi, Osaka (JP)

(72) Inventors: Naveed Shams, Emeryville, CA (US); Henk-Andre Kroon, Emeryville, CA (US); Hisashi Kawata, Osaka (JP); Noriko Kawabata, Osaka (JP)

(73) Assignee: SANTEN PHARMACEUTICAL CO., LTD., Osaka-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/212,592

(22) Filed: Jul. 18, 2016

(65) Prior Publication Data

US 2016/0324838 A1    Nov. 10, 2016

Related U.S. Application Data

(63) Continuation of application No. 14/592,167, filed on Jan. 8, 2015, now Pat. No. 9,415,038.

(60) Provisional application No. 61/925,882, filed on Jan. 10, 2014.

(51) Int. Cl.
*A61K 31/444* (2006.01)
*A61K 9/00* (2006.01)

(52) U.S. Cl.
CPC .......... *A61K 31/444* (2013.01); *A61K 9/0048* (2013.01)

(58) Field of Classification Search
None
See application file for complete search history.

(56) References Cited

U.S. PATENT DOCUMENTS

| | | |
|---|---|---|
| 2011/0054172 A1 | 3/2011 | Iwamura et al. |
| 2012/0190852 A1 | 7/2012 | Hagihara et al. |
| 2014/0018350 A1 | 1/2014 | Kirihara et al. |
| 2014/0018396 A1 | 1/2014 | Kirihara et al. |
| 2014/0113907 A1 | 4/2014 | Iwamura et al. |
| 2016/0317512 A1 | 11/2016 | Endo |
| 2016/0317664 A1 | 11/2016 | Endo |

FOREIGN PATENT DOCUMENTS

| | | |
|---|---|---|
| EP | 2415763 A1 | 2/2012 |
| EP | 3093019 A1 | 11/2016 |
| JP | 2011-57633 A | 3/2011 |
| JP | 2014-019650 A | 2/2014 |
| WO | WO 2009/113600 A1 | 9/2009 |
| WO | WO 2010/113957 A1 | 10/2010 |
| WO | WO 2014/010654 A2 | 1/2014 |

OTHER PUBLICATIONS

Office Action issued by the Japanese Patent Office in corresponding Japanese Patent Application No. 2015-527691 dated Aug. 10, 2015 (3 pages).

Extended Search Report issued by the European Patent Office in corresponding European Patent Application No. 15735133.9 dated Aug. 11, 2017 (7 pages).

*Primary Examiner* — Samantha L Shterengarts

(74) *Attorney, Agent, or Firm* — Buchanan, Ingersoll & Rooney PC

(57) ABSTRACT

Provided is a pharmaceutical preparation for treatment or prevention of glaucoma or ocular hypertension, comprising 0.0003 to 0.01% (w/v) of isopropyl (6-{[4-(pyrazol-1-yl) benzyl] (pyridin-3-ylsulfonyl)aminomethyl}pyridin-2-ylamino) acetate, or a salt thereof. The pharmaceutical preparation has an excellent intraocular pressure lowering effect and may be used as a therapeutic or preventive agent for glaucoma or ocular hypertension or an intraocular pressure lowering agent.

15 Claims, No Drawings

PHARMACEUTICAL FORMULATIONS COMPRISING A PYRIDYLAMINOACETIC ACID COMPOUND

TECHNICAL FIELD

The present invention relates to a pharmaceutical preparation containing isopropyl (6-{[4-(pyrazol-1-yl)benzyl](pyridin-3-yl-sulfonyl) aminomethyl}pyridin-2-ylamino)acetate or a salt thereof.

BACKGROUND ART

Isopropyl 6-{[4-(pyrazol-1-yl)benzyl](pyridin-3-ylsulfonyl) aminomethyl}pyridin-2-ylamino) acetate is a compound represented by the following formula (1), and is described as one of an enormous number of pyridylaminoacetic acid compounds in Patent Literature 1.

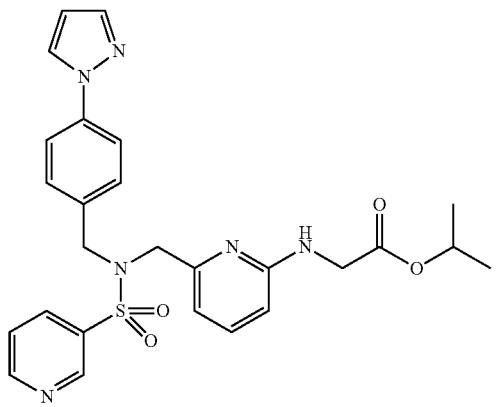

(1)

Also, such an enormous number of pyridylaminoacetic acid compounds have an EP2 agonistic activity (refer to Patent Literature 2) and are thus expected to have an intraocular pressure lowering effect, and a suggestion has been made that the compounds may be used as therapeutic agents for glaucoma (refer to Patent Literature 1). Note that the entire contents of Patent Literatures 1 and 2 are incorporated herein by reference.

However, there is no description about which of such an enormous number of pyridylaminoacetic acid compounds has an especially excellent intraocular pressure lowering effect and may be used as a therapeutic or preventive agent for glaucoma, and there is no description at all about how the intraocular pressure lowering effect is influenced by the content of the compounds.

CITATION LIST

Patent Literature

[Patent Literature 1] US Patent Application Publication No. 2012/0190852
[Patent Literature 2] US Patent Application Publication No. 2011/0054172

SUMMARY OF INVENTION

An object of the present invention is to find which of an enormous number of pyridylaminoacetic acid compounds has an especially excellent intraocular pressure lowering effect and may be used as a therapeutic or preventive agent for glaucoma or ocular hypertension or an intraocular pressure lowering agent, and to find how the found compound is used and/or what dose of the compound is administrated to a patient (mainly, a human) in order to obtain an effective therapeutic or preventive effect.

To achieve the above-described objects, the present inventors have conducted earnest studies. As a result, the inventors have found out that isopropyl (6-{[4-(pyrazol-1-yl)benzyl] (pyridin-3-yl-sulfonyl) aminomethyl}pyridin-2-ylamino) acetate or a salt thereof (hereinafter also referred to as "present compound") has an excellent intraocular pressure lowering effect and may be used as a therapeutic or preventive agent for glaucoma or ocular hypertension or an intraocular pressure lowering agent. Further, the inventors have found out that a somewhat low content of the present compound exhibits a more excellent intraocular pressure lowering effect than a high content of the present compound, and surprisingly, an especially excellent intraocular pressure lowering effect is exhibited when one or two drops of an eye drop containing the present compound at a concentration of from 0.001 to 0.01% (w/v), preferably from 0.001 to 0.003% (w/v) are instilled to a human once or twice a day, and such a usage and/or dose achieves an effective therapeutic or preventive effect, and the inventors have brought the present invention into completion. As employed herein, the term "% (w/v)" refers to the mass (g) of an effective ingredient (here, the present compound) or an additive (e.g. a surfactant, etc.) contained in 100 mL of an ophthalmic solution. For example, 0.01% (w/v) of the present compound means that the content of the present compound in 100 mL of the ophthalmic solution is 0.01 g.

Specifically, the present invention can relate to the followings.

(1) A pharmaceutical preparation for treatment or prevention of a glaucoma or ocular hypertension, comprising 0.001 to 0.01% (w/v) of isopropyl (6-{[4-(pyrazol-1-yl)benzyl] (pyridin-3-ylsulfonyl) aminomethyl}pyridin-2-ylamino) acetate, or a salt thereof.

(2) The pharmaceutical preparation described in (1), comprising 0.001 to 0.003% (w/v) of isopropyl (6-{[4-(pyrazol-1-yl)benzyl] (pyridin-3-ylsulfonyl)aminomethyl}pyridin-2-ylamino) acetate, or a salt thereof.

(3) The pharmaceutical preparation described in (1), comprising 0.0013 to 0.0027% (w/v) of isopropyl (6-{[4-(pyrazol-1-yl)benzyl] (pyridin-3-ylsulfonyl) aminomethyl}pyridin-2-ylamino) acetate, or a salt thereof.

(4) The pharmaceutical preparation described in (1), comprising 0.0015 to 0.0025% (w/v) of isopropyl (6-{[4-(pyrazol-1-yl)benzyl] (pyridin-3-ylsulfonyl) aminomethyl}pyridin-2-ylamino) acetate, or a salt thereof.

(5) The pharmaceutical preparation described in any one of (1) to (4), in which a dosage form is an eye drop.

(6) The pharmaceutical preparation described in any one of (1) to (5), in which the pharmaceutical preparation is used for a human.

(7) The pharmaceutical preparation described in any one of (1) to (6), in which the pharmaceutical preparation is used to be instilled once or twice a day.

(8) The pharmaceutical preparation described in (7), in which the pharmaceutical preparation is used in such a manner that a dose of one or two drops is instilled.

(9) The pharmaceutical preparation described in any one of (1) to (6), in which the pharmaceutical preparation is used to be instilled once a day.

(10) The pharmaceutical preparation described in (9), in which the pharmaceutical preparation is used in such a manner that a dose of one drop is instilled.

The present invention provides a pharmaceutical preparation for treatment or prevention of glaucoma or ocular hypertension, or for lowering of intraocular pressure, in which the present compound contains the dose described in (1) to (10) and/or is administered according to the usage described in (1) to (10) thereby to have an excellent intraocular pressure lowering effect for a patient, particularly a human.

The present invention also provides a method for treatment or prevention of glaucoma or ocular hypertension, and a method for lowering an intraocular pressure, using the pharmaceutical preparation.

The present invention further provides a method for using the present compound in order to prepare a pharmaceutical preparation for treatment or prevention of glaucoma or ocular hypertension, or for lowering of intraocular pressure.

DESCRIPTION OF EMBODIMENTS

Embodiments of the present invention will be described in detail below.

Isopropyl(6-{[4-(pyrazol-1-yl)benzyl] (pyridin-3-ylsulfonyl) aminomethyl}pyridin-2-ylamino)acetate or a salt thereof, contained in a therapeutic or preventive agent for glaucoma or ocular hypertension or an intraocular pressure lowering agent (hereinafter also referred to as "medicament"), according to the present invention, can be prepared by a method described in US Patent Application Publication No. 2012/0190852 (Patent Literature 1), a typical method in the technical field thereof, or the like.

A salt of isopropyl(6-{[4-(pyrazol-1-yl)benzyl] (pyridin-3-ylsulfonyl)aminomethyl}pyridin-2-ylamino)acetate contained in the medicament of the present invention is not particularly limited as long as it is a pharmaceutically acceptable salt. Specifically, examples of the salt include inorganic acid salts such as hydrochloride, hydrobromide, hydroiodide, nitrate, sulfate or phosphate; or organic acid salts such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate or aspartate, preferably hydrochloride or trifluoroacetate.

The content of isopropyl(6-{[4-(pyrazol-1-yl)benzyl] (pyridin-3-ylsulfonyl) aminomethyl}pyridin-2-ylamino) acetate or the salt thereof contained in the medicament of the present invention is not particularly limited as long as it lies between 0.001 and 0.01% (w/v). Specifically, its lower limit is preferably 0.001% (w/v), more preferably 0.0013% (w/v), or still more preferably 0.0015% (w/v). Its upper limit is preferably 0.01% (w/v), more preferably 0.005% (w/v), still more preferably 0.003% (w/v), more particularly preferably 0.0027% (w/v), or most preferably 0.0025% (w/v). More particularly, the content is preferably from 0.001 to 0.005% (w/v), more preferably from 0.001 to 0.003% (w/v), still more preferably from 0.0013 to 0.0027% (w/v), or most preferably from 0.0015 to 0.0025% (w/v). More specifically, the content is preferably 0.0010% (w/v), 0.0011% (w/v), 0.0012% (w/v), 0.0013% (w/v), 0.0014% (w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028% (w/v), 0.0029% (w/v), 0.0030% (w/v), 0.005% (w/v), or 0.01% (w/v).

When the salt of isopropyl(6-{[4-(pyrazol-1-yl)benzyl] (pyridin-3-ylsulfonyl)aminomethyl}pyridin-2-ylamino)acetate is contained, the content of isopropyl (6-{[4-(pyrazol-1-yl)benzyl] (pyridin-3-ylsulfonyl)aminomethyl}pyridin-2-ylamino)acetate with the salt released is in the above-described range.

If necessary, an additive may be used in the medicament of the present invention. A surfactant, a buffer, a tonicity agent, a stabilizer, a preservative, an anti-oxidant, a polymer of high-molecular weight, or the like, for example, may be added as the additive.

A surfactant usable as an additive for medicines may be appropriately mixed in the medicament of the present invention. Examples of the surfactant include polyoxyethylene castor oil, polyoxyethylene hydrogenated castor oil, polyoxyethylene sorbitan fatty acid ester, vitamin E, TPGS, polyoxyethylene fatty acid ester, polyoxyethylene polyoxypropylene glycol, sucrose fatty acid ester, and the like.

More specifically, various polyoxyethylene castor oils having different numbers of polymerization of ethylene oxide may be used as the polyoxyethylene castor oil, and the number of polymerization of ethylene oxide is preferably from 5 to 100, more preferably from 20 to 50, particularly preferably from 30 to 40, or most preferably 35. Specific examples of the polyoxyethylene castor oil include polyoxyl 5 castor oil, polyoxyl 9 castor oil, polyoxyl 15 castor oil, polyoxyl 35 castor oil, polyoxyl 40 castor oil, and the like, and polyoxyl 35 castor oil is most preferable.

Various polyoxyethylene hydrogenated castor oils having different numbers of polymerization of ethylene oxide may be used as the polyoxyethylene hydrogenated castor oil, and the number of polymerization of ethylene oxide is preferably from 10 to 100, more preferably from 20 to 80, particularly preferably from 40 to 70, or most preferably 60. Specific examples of the polyoxyethylene hydrogenated castor oil include polyoxyethylene hydrogenated castor oil 10, polyoxyethylene hydrogenated castor oil 40, polyoxyethylene hydrogenated castor oil 50, polyoxyethylene hydrogenated castor oil 60, and the like, and polyoxyethylene hydrogenated castor oil 60 is most preferable.

Examples of the polyoxyethylene sorbitan fatty acid ester include Polysorbate 80, Polysorbate 60, Polysorbate 40, polyoxyethylene sorbitan monolaurate, polyoxyethylene sorbitan triolate, Polysorbate 65, and the like, and Polysorbate 80 is most preferable.

Vitamin E and TPGS are also referred to as tocopherol polyethylene glycol 1000 succinate.

Examples of the polyoxyethylene fatty acid ester include polyoxyl stearate 40, and the like.

Examples of the polyoxyethylene polyoxypropylene glycol include polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like.

Examples of the sucrose fatty acid ester include sucrose stearate, and the like.

When the surfactant is mixed in the medicament of the present invention, the content of the surfactant may be appropriately adjusted according to the type of the surfactant, or the like. Specifically, its lower limit is preferably 0.001% (w/v), more preferably 0.01% (w/v), still more preferably 0.1% (w/v), or particularly preferably 0.5% (w/v). Its upper limit is preferably is preferably 10% (w/v), more preferably 5% (w/v), still more preferably 4% (w/v), or particularly preferably 3% (w/v). More specifically, the content is preferably from 0.001 to 10% (w/v), more preferably from 0.01 to 5% (w/v), still more preferably from 0.1 to 4% (w/v), or particularly preferably from 0.5 to 3% (w/v).

A buffer usable as an additive for medicines may be appropriately mixed in the medicament of the present invention.

Examples of the buffer include phosphoric acid or a salt thereof, boric acid or a salt thereof, citric acid or a salt thereof, acetic acid or a salt thereof, carbonic acid or a salt thereof, tartaric acid or a salt thereof, ε-aminocaproic acid, trometamol, and the like. More specifically, examples of phosphate include sodium phosphate, sodium dihydrogen phosphate, disodium hydrogenphosphate, potassium phosphate, potassium dihydrogenphosphate, dipotassium hydrogenphosphate, and the like. Examples of borate include borax, sodium borate, potassium borate, and the like. Examples of citrate include sodium citrate, disodium citrate, trisodium citrate, and the like. Examples of acetate include sodium acetate, potassium acetate, and the like. Examples of carbonate include sodium carbonate, sodium hydrogencarbonate, and the like. Examples of tartrate include sodium tartrate, potassium tartrate, and the like. Above all, the boric acid or the salt thereof or the citric acid or the salt thereof is preferable.

When the buffer is mixed in the medicament of the present invention, the content of the buffer may be appropriately adjusted according to the type of the buffer, or the like. The content of the buffer is preferably from 0.001 to 10% (w/v), more preferably from 0.01 to 5% (w/v), still more preferably from 0.1 to 3% (w/v), or most preferably from 0.2 to 2% (w/v).

A tonicity agent usable as an additive for medicines may be appropriately mixed in the medicament of the present invention.

Examples of the tonicity agent include an ionic tonicity agent, a nonionic tonicity agent, and the like.

Examples of the ionic tonicity agent include sodium chloride, potassium chloride, calcium chloride, magnesium chloride, and the like, and examples of the nonionic tonicity agent include glycerin, propylene glycol, sorbitol, mannitol, and the like. When the tonicity agent is mixed in the medicament of the present invention, the content of the tonicity agent may be appropriately adjusted according to the type of the tonicity agent, or the like. The content of the tonicity agent is preferably from 0.01 to 10% (w/v), more preferably from 0.02 to 7% (w/v), still more preferably from 0.1 to 5% (w/v), particularly preferably from 0.5 to 4% (w/v), or most preferably from 0.8 to 3% (w/v).

A stabilizer usable as an additive for medicines may be appropriately mixed in the medicament of the present invention.

Examples of the stabilizer include edetic acid, disodium edetate, tetrasodium edetate, sodium citrate, and the like, and disodium edetate is particularly preferable. Disodium edetate may be a hydrate. When the stabilizer is mixed in the medicament of the present invention, the content of the stabilizer may be appropriately adjusted according to the type of the stabilizer, or the like. The content of the stabilizer is preferably from 0.001 to 1% (w/v), more preferably from 0.005 to 0.5% (w/v), or most preferably from 0.01 to 0.1% (w/v).

A preservative usable as an additive for medicines may be appropriately mixed in the medicament of the present invention.

Examples of the preservative include benzalkonium chloride, benzalkonium bromide, benzetonium chloride, sorbic acid, potassium sorbate, methyl paraoxybenzoate, propyl paraoxybenzoate, chlorobutanol, and the like. When the preservative is mixed in the medicament of the present invention, the content of the preservative may be appropriately adjusted according to the type of the preservative, or the like. The content of the preservative is preferably from 0.0001 to 1% (w/v), more preferably from 0.0005 to 0.1% (w/v), still more preferably from 0.001 to 0.05% (w/v), or most preferably from 0.005 to 0.010% (w/v).

An anti-oxidant usable as an additive for medicines may be appropriately mixed in the medicament of the present invention.

Examples of the anti-oxidant include ascorbic acid, tocopherol, dibutyl hydroxytoluene, butyl hydroxyanisole, sodium erythorbate, propyl gallate, sodium sulfite, and the like. When the anti-oxidant is mixed in the medicament of the present invention, the content of the anti-oxidant may be appropriately adjusted according to the type of the anti-oxidant, or the like. The content of the preservative is preferably from 0.0001 to 1% (w/v), more preferably from 0.0005 to 0.1% (w/v), or most preferably from 0.001 to 0.05% (w/v).

A polymer of high-molecular weight usable as an additive for medicines may be appropriately mixed in the medicament of the present invention.

Examples of the polymer of high-molecular weight include methyl cellulose, ethyl cellulose, hydroxymethyl cellulose, hydroxyethyl cellulose, hydroxypropyl cellulose, hydroxyethyl methyl cellulose, hydroxypropyl methyl cellulose, carboxymethyl cellulose, carboxymethyl cellulose sodium, hydroxypropyl methyl cellulose acetate succinate, hydroxypropyl methyl cellulose phthalate, carboxymethyl ethyl cellulose, cellulose acetate phthalate, polyvinylpyrrolidone, polyvinylalcohol, carboxyvinyl polymer, polyethylene glycol, and the like.

When the polymer of high-molecular weight is mixed in the medicament of the present invention, the content of the polymer of high-molecular weight may be appropriately adjusted according to the type of the polymer of high-molecular weight, or the like. The content of the polymer of high-molecular weight is preferably from 0.001 to 5% (w/v), more preferably from 0.01 to 1% (w/v), or most preferably from 0.1 to 0.5% (w/v).

The pH of the medicament of the present invention is preferably from 4.0 to 8.0, more preferably from 4.5 to 7.5, or most preferably from 5.0 to 7.0. Hydrochloric acid, phosphoric acid, citric acid, acetic acid, sodium hydroxide, potassium hydroxide, or the like, for example, as a pH adjusting agent for adjusting the pH, may be added to the medicament of the present invention.

The medicament of the present invention can be filled into and preserved in containers made of various materials. A container made of polyethylene, polypropylene, or the like, for example, may be used, and preferably, the medicament of the present invention is filled into and preserved in the container made of polyethylene from the viewpoint of ease of instillation (or hardness of the container) or the like.

A dosage form of the medicament of the present invention is not particularly limited as long as it is usable for medicines. Specifically, examples of the dosage form include an eye drop, an ophthalmic injection, an ophthalmic ointment, and the like, and the eye drop is particularly preferable. These dosage forms of the medicament can be prepared according to ordinary methods in the art. Also, when the medicament of the present invention is a liquid medicament, it is preferable that a solvent or a dispersion medium be water.

The medicament of the present invention may contain one or more, preferably one to three, or more preferably one or two other therapeutic agents for glaucoma or ocular hypertension or intraocular pressure lowering agents, and other therapeutic agents for glaucoma are not particularly limited. Specifically, a therapeutic agent for glaucoma or the like which is commercially available or under development is preferable, a commercially available therapeutic agent for glaucoma or the like is more preferable, or a commercially available therapeutic agent for glaucoma or the like which is different in function and mechanism from the present compound is particularly preferable.

The usage of the medicament of the present invention is not particularly limited as long as it is sufficient to achieve a desired pharmacological effect, and the usage of the medicament may be appropriately selected according to symptoms of a disease, the age or body weight of a patient, the dosage form of the medicament, or the like.

Specifically, a dose of one to five drops, preferably one to three drops, more preferably one or two drops, or particularly preferably one drop may be instilled every day through every week one to four times a day, preferably one to three times a day, more preferably once or twice a day, or particularly preferably once a day. Most preferably, a dose of one drop is instilled every day once a day. Here, one drop is typically from about 0.01 to about 0.1 mL, preferably from about 0.015 to about 0.07 mL, more preferably from about 0.02 to about 0.05 mL, or particularly preferably from about 0.03 mL.

The medicament of the present invention refers to a therapeutic or preventive agent, and more specifically to a therapeutic or preventive agent for glaucoma, a therapeutic or preventive agent for ocular hypertension, or an intraocular pressure lowering agent.

Glaucoma in the present invention includes primary open angle glaucoma, secondary open angle glaucoma, normal tension glaucoma, hypersecretion glaucoma, primary angle-closure glaucoma, secondary angle-closure glaucoma, plateau iris glaucoma, combined-mechanism glaucoma, developmental glaucoma, steroid-induced glaucoma, exfoliation glaucoma, amyloid glaucoma, neovascular glaucoma, malignant glaucoma, capsular glaucoma, plateau iris syndrome, and the like, or preferably primary open angle glaucoma, normal tension glaucoma, and primary angle-closure glaucoma, and the pharmaceutical preparation of the present invention is particularly effective for primary open angle glaucoma.

EXAMPLES

Although preparation examples and clinical test results will be given below, they are for purposes of a better understanding of the present invention and are not intended to limit the scope of the present invention.

Preparation Examples

Representative preparation examples of the medicament of the present invention will be given below. In the following preparation examples, the amounts of ingredients mixed are the contents thereof in 100 mL of a preparation. The present compound A refers to isopropyl(6-{[4-(pyrazol-1-yl)benzyl] (pyridin-3-ylsulfonyl)amino methyl}pyridin-2-ylamino)acetate.

Preparation Example 1

| Eye Drop (in 100 mL) | |
| --- | --- |
| Present compound A | 0.002 g |
| Boric acid | 0.2 g |
| Glycerin | 2.0 g |
| Polysorbate 80 | 0.5 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 2

| Eye Drop (in 100 mL) | |
| --- | --- |
| Present compound A | 0.002 g |
| Sodium dihydrogen phosphate | 0.2 g |
| Glycerin | 2.0 g |
| Vitamin E, TPGS | 0.8 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 3

| Eye Drop (in 100 mL) | |
| --- | --- |
| Present compound A | 0.002 g |
| Trisodium citrate | 0.2 g |
| Glycerin | 2.0 g |
| Polyoxyethylene hydrogenated castor oil 60 | 0.3 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

In Preparation Examples 1 to 3, a medicament can be obtained by appropriately adjusting the type and/or mixed amount of the present compound A and/or the additive.

1. Clinical Test (1)

1-1. Preparation of Eye Drop

Eye drops 1 and 2 and a placebo eye drop given in Table 1 were prepared.

TABLE 1

| | % (w/v) | | |
| --- | --- | --- | --- |
| | Eye drop 1 | Eye drop 2 | Placebo eye drop |
| Present compound A | 0.003 | 0.01 | — |
| Disodium edetate dihydrate | 0.05 | 0.05 | 0.05 |
| Sorbic acid | 0.1 | 0.1 | 0.1 |
| Polyoxyl 35 castor oil | 0.8 | 1.7 | 5 |
| Boric acid | 1 | 1 | 1 |

TABLE 1-continued

| | % (w/v) | | |
|---|---|---|---|
| | Eye drop 1 | Eye drop 2 | Placebo eye drop |
| Glycerin | 1 | 1 | 1 |
| Benzalkonium chloride | 0.01 | 0.01 | 0.01 |
| HCl/NaOH | q.s. | q.s. | q.s. |
| Purified water | q.s. | q.s. | q.s. |
| pH | About 6.5 | About 6.5 | About 6.5 |

1-2. Test Method

For primary open angle glaucoma patients (26 persons) or ocular hypertension patients (18 persons), one drop (about 0.03 ml) of the eye drops 1 and 2 or the placebo eye drop was instilled once a day for four weeks.

1-3. Test Results and Discussion

An average intraocular pressure change (mmHg) from before the start of instillation of the eye drops 1 and 2 (or a base line), after a lapse of 16 hours after the last instillation, was calculated as a difference from an average intraocular pressure change of the placebo eye drop. Results are shown in Table 2.

TABLE 2

Average intraocular pressure change (mmHg) after a lapse of 16 hours after the last instillation (relative to placebo eye drop)

| Eye drop 1 | −4.6 |
|---|---|
| Eye drop 2 | −2.5 |

As is apparent from Table 2, the eye drop 1 (0.003%) and the eye drop 2 (0.01%) both exhibit an intraocular pressure lowering effect, and exhibited a more excellent intraocular pressure lowering effect when the content of the present compound A is 0.003% (w/v). On the contrary to expectation of those skilled in the art, a significantly low content of the present compound A exhibited a higher intraocular pressure lowering effect.

2. Clinical Test (2)

2-1. Preparation of Eye Drop

Eye drops 3 to 6 and a placebo eye drop given in Table 3 were prepared. The eye drop 3 contains 0.0003% (w/v) of the present compound A and thus is Reference Example of the present invention.

TABLE 3

| | % (w/v) | | | | |
|---|---|---|---|---|---|
| | Eye drop 3 | Eye drop 4 | Eye drop 5 | Eye drop 6 | Placebo eye drop |
| Present compound A | 0.0003 | 0.001 | 0.002 | 0.003 | — |
| Disodium edetate dihydrate | 0.02 | 0.02 | 0.02 | 0.02 | 0.02 |
| Polyoxyl 35 castor oil | 0.8 | 0.8 | 0.8 | 0.8 | 0.8 |
| Boric acid | 1 | 1 | 1 | 1 | 1 |
| Glycerin | 1 | 1 | 1 | 1 | 1 |
| Benzalkonium chloride | 0.01 | 0.01 | 0.01 | 0.01 | 0.01 |
| HCl/NaOH | q.s. | q.s. | q.s. | q.s. | q.s. |
| Purified water | q.s. | q.s. | q.s. | q.s. | q.s. |
| pH | About 6 | About 6 | About 6 | About 6 | About 6 |

2-2. Test Method

For primary open angle glaucoma patients (37 persons) or ocular hypertension patients (39 persons), one drop (about 0.03 ml) of the eye drops 3 to 6 or the placebo eye drop was instilled once a day for four weeks.

2-3. Test Results and Discussion

An average intraocular pressure change (mmHg) from before the start of instillation of the eye drops 1 and 2 (or a base line), after a lapse of 16 hours after the last instillation, was calculated as a difference from an average intraocular pressure change of the placebo eye drop. Results are shown in Table 4.

TABLE 4

Average intraocular pressure change (mmHg) after a lapse of 16 hours after the last instillation (relative to placebo eye drop)

| Eye drop 3 | −1.9 |
|---|---|
| Eye drop 4 | −3.1 |
| Eye drop 5 | −5.2 |
| Eye drop 6 | −4.0 |

As is apparent from Table 4, the eye drops 4 to 6 all exhibited a higher intraocular pressure lowering effect than the eye drop 3. Therefore, when the content of the present compound A is from 0.001 to 0.003% (w/v) like the eye drops 4 to 6, a particularly excellent intraocular pressure lowering effect was exhibited.

The invention claimed is:

1. A pharmaceutical preparation for treatment or prevention of glaucoma or ocular hypertension, comprising 0.001 to 0.003% (w/v) of isopropyl(6-{[4-(pyrazol-1-yl)benzyl](pyridin-3-ylsulfonyl)aminomethyl}pyridin-2-ylamino)acetate, or a salt thereof, wherein the pH of the preparation is from 4.0 to 8.0.

2. The pharmaceutical preparation of claim 1, comprising 0.0011 to 0.0030% (w/v) of isopropyl(6-{[4-(pyrazol-1-yl)benzyl](pyridin-3-ylsulfonyl)aminomethyl}pyridin-2-ylamino)acetate, or a salt thereof.

3. The pharmaceutical preparation of claim 1, comprising 0.0011 to 0.0029% (w/v) of isopropyl(6-{[4-(pyrazol-1-yl)benzyl](pyridin-3-ylsulfonyl)aminomethyl}pyridin-2-ylamino)acetate, or a salt thereof.

4. The pharmaceutical preparation of claim 1, comprising 0.0013 to 0.0027% (w/v) of isopropyl(6-{[4-(pyrazol-1-yl)benzyl](pyridin-3-ylsulfonyl)aminomethyl}pyridin-2-ylamino)acetate, or a salt thereof.

5. The pharmaceutical preparation of claim 1, comprising 0.0015 to 0.0025% (w/v) of isopropyl(6-{[4-(pyrazol-1-yl)benzyl](pyridin-3-ylsulfonyl)aminomethyl}pyridin-2-ylamino)acetate, or a salt thereof.

6. The pharmaceutical preparation of claim 1, comprising 0.0010% (w/v), 0.0011% (w/v), 0.0012% (w/v), 0.0013% (w/v), 0.0014% (w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028% (w/v), 0.0029% (w/v) or 0.0030% (w/v) of isopropyl(6-{[4-(pyrazol-1-yl)benzyl](pyridin-3-ylsulfonyl)aminomethyl}pyridin-2-ylamino)acetate, or a salt thereof.

7. The pharmaceutical preparation of claim 1, comprising 0.0011% (w/v), 0.0012% (w/v), 0.0013% (w/v), 0.0014% (w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028%

(w/v), 0.0029% (w/v) or 0.0030% (w/v) of isopropyl(6-{[4-(pyrazol-1-yl)benzyl](pyridin-3-ylsulfonyl)aminomethyl}pyridin-2-ylamino)acetate, or a salt thereof.

8. The pharmaceutical preparation described in claim 1, comprising 0.0011% (w/v), 0.0012% (w/v), 0.0013% (w/v), 0.0014% (w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028% (w/v) or 0.0029% (w/v) of isopropyl(6-{[4-(pyrazol-1-yl)benzyl](pyridin-3-ylsulfonyl)aminomethyl}pyridin-2-ylamino)acetate, or a salt thereof.

9. An eye drop comprising the pharmaceutical preparation of claim 1.

10. A method for treatment or prevention of glaucoma or ocular hypertension, comprising administrating the pharmaceutical preparation of claim 1 to a patient who needs the treatment or prevention of glaucoma or ocular hypertension.

11. The method of claim 10, in which the administrating is instillation.

12. The method of claim 11, in which the instillation is provided once or twice a day.

13. The method of claim 10, in which a dose of one or two drops is instilled.

14. The method of claim 10, in which a dose of one drop is instilled once a day.

15. The method of claim 10, wherein the patient is a human.

* * * * *